United States Patent
Kishii et al.

(10) Patent No.: US 10,961,495 B2
(45) Date of Patent: Mar. 30, 2021

(54) CELL STRUCTURE PRODUCING APPARATUS

(71) Applicant: Cyfuse Biomedical K.K., Tokyo (JP)

(72) Inventors: Yasuto Kishii, Tokyo (JP); Norihiko Tokunaga, Tokyo (JP)

(73) Assignee: CYFUSE BIOMEDICAL K.K., Tokyo (JP)

( * ) Notice: Subject to any disclaimer, the term of this patent is extended or adjusted under 35 U.S.C. 154(b) by 144 days.

(21) Appl. No.: 16/308,343

(22) PCT Filed: Oct. 30, 2017

(86) PCT No.: PCT/JP2017/039168
§ 371 (c)(1),
(2) Date: Dec. 7, 2018

(87) PCT Pub. No.: WO2019/087262
PCT Pub. Date: May 9, 2019

(65) Prior Publication Data
US 2019/0359929 A1    Nov. 28, 2019

(51) Int. Cl.
*C12M 1/26*  (2006.01)
*C12N 5/00*  (2006.01)
*C12M 3/00*  (2006.01)
*B33Y 30/00*  (2015.01)
*B33Y 40/00*  (2020.01)
*B33Y 70/00*  (2020.01)
*C12N 5/07*  (2010.01)

(52) U.S. Cl.
CPC ............. *C12M 33/04* (2013.01); *B33Y 30/00* (2014.12); *B33Y 40/00* (2014.12); *B33Y 70/00* (2014.12); *C12M 21/08* (2013.01); *C12N 5/0062* (2013.01); *C12N 5/06* (2013.01); *C12N 2513/00* (2013.01); *C12N 2535/00* (2013.01)

(58) Field of Classification Search
None
See application file for complete search history.

(56) References Cited

U.S. PATENT DOCUMENTS

| | | | |
|---|---|---|---|
| 8,198,086 B2 | 6/2012 | Koga et al. | |
| 10,087,415 B2 | 10/2018 | Kuchiishi et al. | |
| 2011/0200559 A1 | 8/2011 | Koga et al. | |
| 2012/0083029 A1* | 4/2012 | Tsumura ................ | C12M 21/08 435/289.1 |

FOREIGN PATENT DOCUMENTS

| | | |
|---|---|---|
| JP | 4517125 B2 | 8/2010 |
| WO | WO 2008/123614 A1 | 10/2008 |
| WO | WO 2016/047737 A1 | 3/2016 |
| WO | WO 2017/134787 A1 | 8/2017 |

OTHER PUBLICATIONS

European Search Report, dated Aug. 19, 2019, for European Application No. 17911399.8.
Moldovan et al., "Principles of the Kenzan Method for Robotic Cell Spheroid-Based Three-Dimensional Bioprinting," Tissue Engineering: Part B, vol. 23, No. 3, Jun. 1, 2017, (Downloaded by EPO on Jun. 18, 2019), XP55597418, pp. 237-244 (Total pages 11).
English translation of Written Opinion of the International Searching Authority (PCT/ISA/237) issued in PCT/JP2017/039168, dated Jan. 23, 2018.
International Search Report (PCT/ISA/210) issued in PCT/JP2017/039168, dated Jan. 23, 2018.
Ishihara et al., "Simultaneous regeneration of full-thickness cartilage and subchondral bone defects in vivo using a three-dimensional scaffold-free autologous construct derived from high-density bone marrow-derived mesenchymal stem cells," Journal of Orthopaedic Surgery and Research, 2014, 9:98, pp. 1-10.
Kuchiishi, "Regeneration of thick tissue using novel bio 3D printing technologies," 2014, vol. 13 No. 2, pp. 57-59.
Regenerative Medicine, vol. 16, Supple. 2017, 2 pages.
Written Opinion of the International Searching Authority (PCT/ISA/237) issued in PCT/JP2017/039168, dated Jan. 23, 2018.

\* cited by examiner

*Primary Examiner* — James D Schultz
(74) *Attorney, Agent, or Firm* — Birch, Stewart, Kolasch & Birch, LLP

(57) ABSTRACT

The cell structure producing apparatus including needles, a sticking unit configured to detachably hold an end portion of each of the needles, descend the each of the needles with respect to a cell tray in which cell aggregates are held, stick and penetrate each of the cell aggregates with the tip end, and ascend the needle after sticking, at least one time or more, a base unit, and a control unit configured to move the sticking unit so that for the each of the needles, each of the needles sticking the cell aggregates is positioned at a predetermined position over the base unit, descend each of the needles by a predetermined amount to stick the tip end into the base unit at the predetermined position on the base unit, and control the sticking unit.

18 Claims, 13 Drawing Sheets

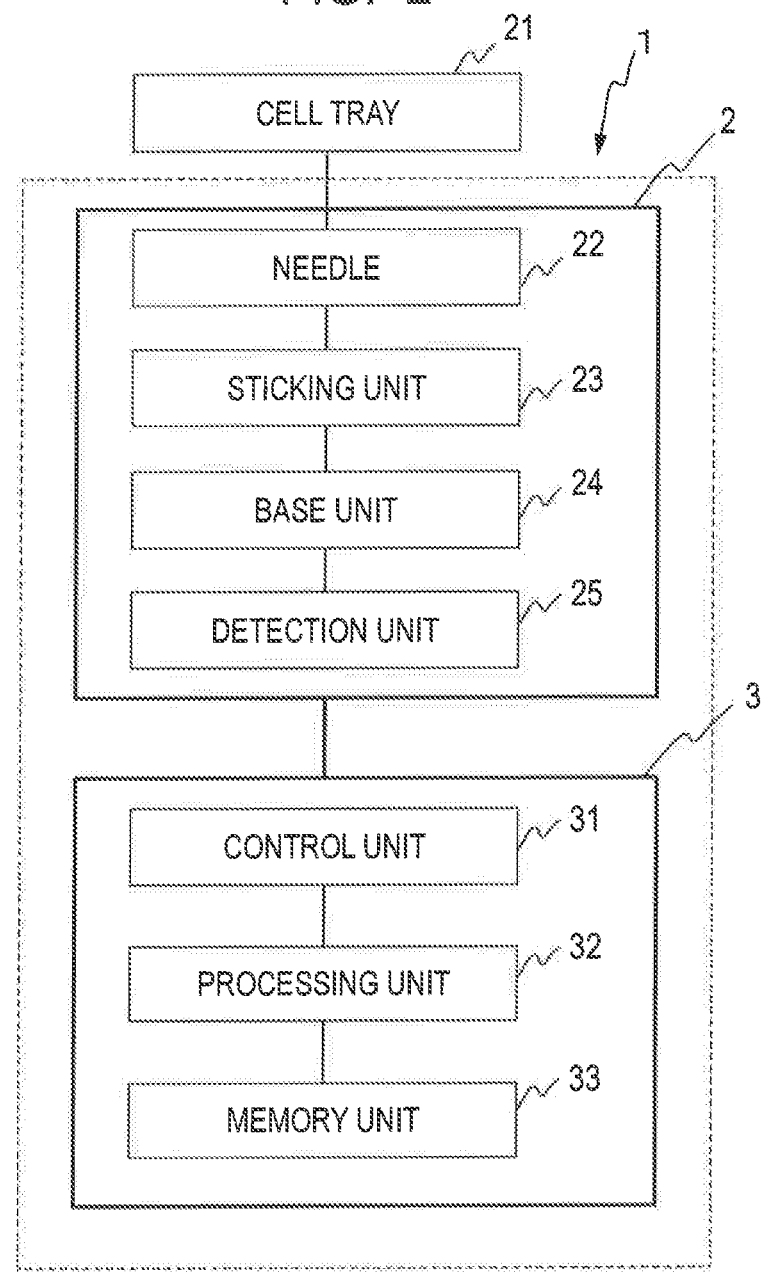

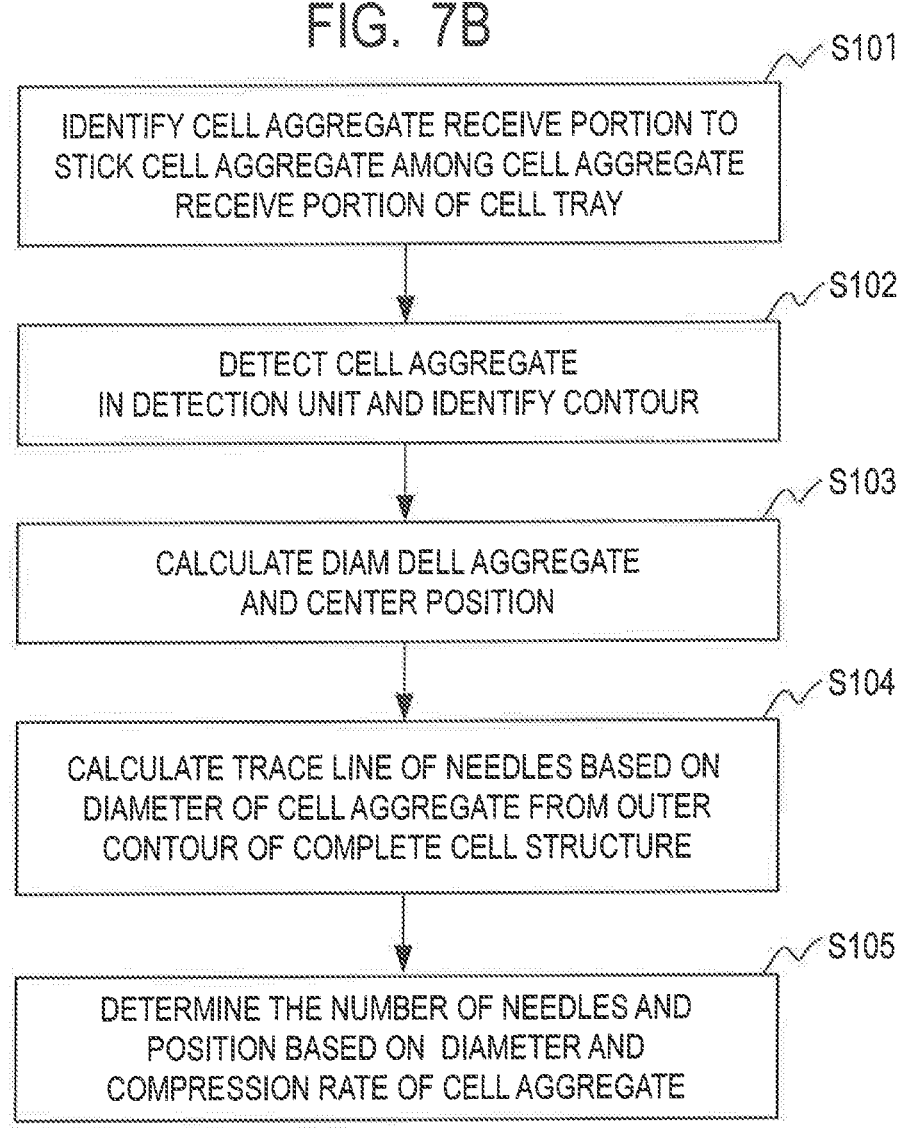

ary, as disclosed in Patent Literature 1, there has been known a method for producing a three-dimensional structure by three-dimensionally stacking cell aggregates so that a plurality of cell aggregates are adjacent to one another by using a support formed of a plurality of needle-shaped bodies fixed in advance to extend in a normal direction of a substrate by virtue of the property that cell aggregates contacting one another to be adjacent to one another are fused. In this method, the cell aggregates are taken out, each of the plurality of cell aggregates held by suction or the like is stuck onto each of the plurality of needle-shaped bodies to produce a support in which the cell aggregates are skewered. The method is such that the cell aggregates are cultivated in this state and the cell aggregates are extracted from the needle-shaped bodies after the cell aggregates are fused to one another, whereby the three-dimensional structure of cells is obtained.

In this relation, Patent Literature 2 discloses a method in which one thin needle-shaped body is caused to ascend and descend in the vertical direction to cell aggregates arranged on a cultivation plate not to move, the one needle-shaped body on which the cell aggregates are skewered is produced, and by repeating this, needle-shaped bodies are aligned in an aligning frame to be cultivated.

CITATION LIST

Patent Literature

PTL 1: Japanese Patent No. 4517125
PTL 2: International Publication WO 2016/047737

SUMMARY OF INVENTION

Technical Problem

In the method disclosed in Patent Literature 1, the needle-shaped bodies are fixed in the predetermined positions of the support in advance, so that the positions where the cell aggregates can be stuck are the positions of the needle-shaped bodies, and the degree of freedom of the position that can be selected as the position of the cell aggregate is low. Further, in this method, the support has to be prepared in advance when a three-dimensional cell structure in a special shape is desired to be produced, and there is the problem that a lead time is long.

In this regard, in the method disclosed in Patent Literature 2, the cell aggregates are stuck with the needle-shaped bodies, and the needle-shaped bodies on which the cell aggregates are skewered are fitted into the aligning frame to be held, so that the degree of freedom of the position that can be selected as the position of the cell aggregate is low due to the set position as the holding unit of the needle-shaped body in the aligning frame. Further, in this method, in the case where the three-dimensional cell structure in a special shape is desired to be produced, the aligning frame adapted to the three-dimensional cell structure in the special shape has to be prepared in advance, and the lead time becomes long as in the method disclosed in Patent Literature 1.

The present invention is made in the light of these problems, and provides a cell structure producing apparatus capable of properly sticking stuck cell aggregates in a desired configuration, and a cell tray that is used in the cell structure producing apparatus.

Solution to Problem

The problems are solved by a cell structure producing apparatus including a plurality of needles elongated and each having a pointed tip end, a sticking unit configured to, with respect to each of the plurality of needles, detachably keep hold of an end portion at an opposite side of the tip end of the needle, cause the needle to descend with respect to a cell tray in which a cell aggregate is held, stick and penetrate the cell aggregate with the tip end, and cause the needle to ascend after sticking, at least one time or more, a base unit having a surface capable of receiving the tip end by the tip end of the needle sticking the surface to hold the needle, and a control unit configured to move the sticking unit so that each of the plurality of needles on which the cell aggregate is stuck is located in a predetermined position on the base unit, with respect to each of the plurality of needles, cause each of the plurality of needles to descend by a predetermined amount to stick the tip end into the base unit in a predetermined position of the base unit, control the sticking unit so that the sticking unit releases the hold after the tip end is stuck in the base unit, and perform alignment of each of the plurality of needles on the base unit.

The problems are solved by a method for producing a cell structure by a cell structure producing apparatus including a plurality of needles elongated and each having a pointed tip end, a sticking unit configured to move the plurality of needles, and a base unit having a surface capable of receiving the tip end by the tip end of the needle sticking the surface to hold the needles, the method including a sticking step of, with respect to one of the plurality of needles, detachably keeping hold of an end portion at an opposite side of the tip end of the needle, causing the needle to descend with respect to a cell tray in which a cell aggregate is held, sticking and penetrating the cell aggregate with the tip end, and causing the needle to ascend after sticking, at least one time or more, and a disposing step of moving one of the plurality of needles on which the cell aggregate is stuck to a predetermined position over the base unit, after the sticking step, causing the one of the plurality of needles to descend by a predetermined amount to stick the tip end into the base unit in the predetermined position of the base unit, and releasing the hold after the tip end is stuck in the base unit, the method performing alignment of the plurality of needles by repeatedly performing the sticking step and the disposing step to all of the plurality of needles so that each of spaces among the plurality of needles held in the base unit becomes a predetermined distance.

Advantageous Effects of Invention

According to the cell tray of the present invention, a degree of freedom of disposition of cell aggregates can be enhanced, in production of the cell structure.

BRIEF DESCRIPTION OF DRAWINGS

FIG. 2 is a configurational block diagram of the cell structure producing apparatus.

FIG. 7B is a flowchart of a process of determining a number of needles to be disposed and positions thereof.

DESCRIPTION OF EMBODIMENTS

Figure 1:
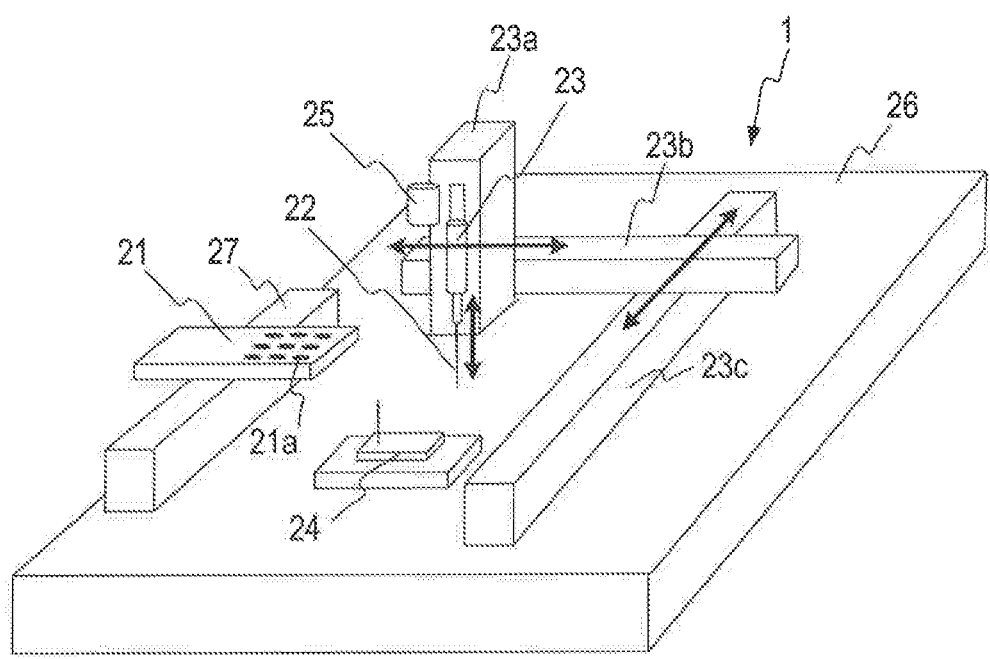
FIG. 1 is a view illustrating a cell structure producing apparatus.
Figure 3A:
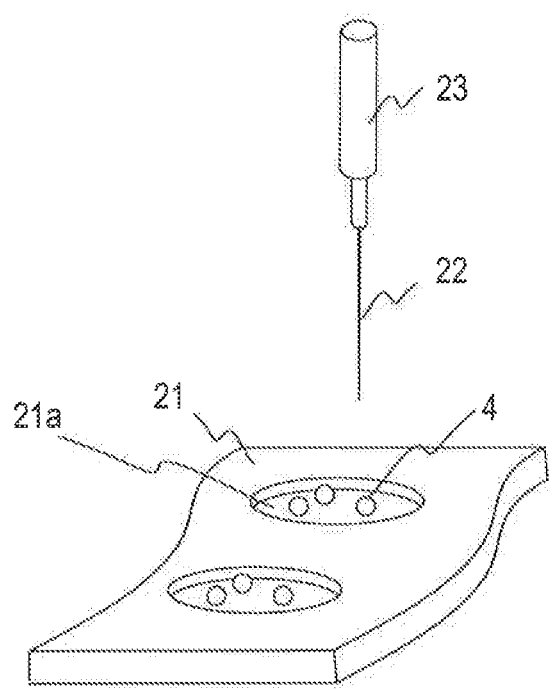
FIG. 3A is a view illustrating a step of sticking a cell aggregate with a needle.
Figure 3B:
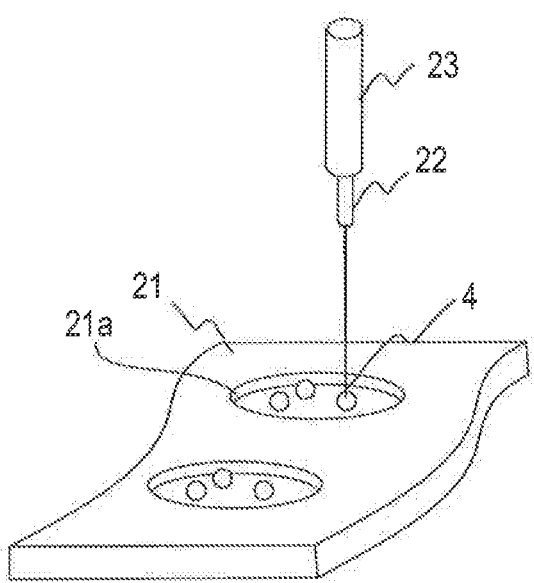
FIG. 3B is a view illustrating the step of sticking the cell aggregate with the needle.
Figure 3C:
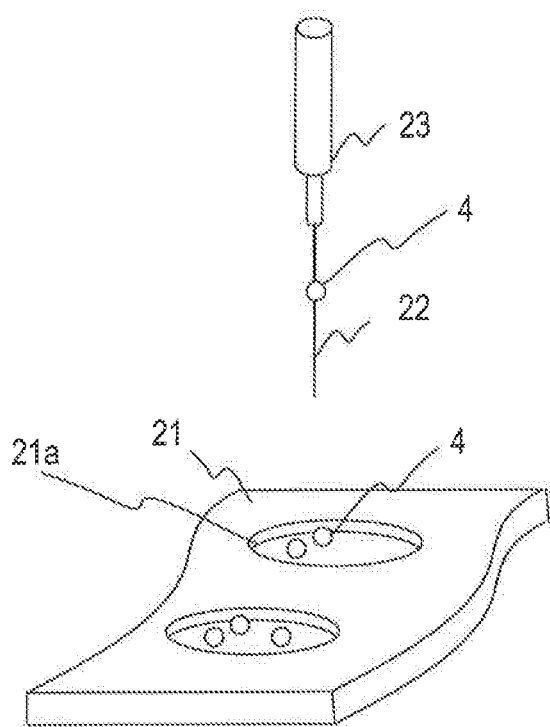
FIG. 3C is a view illustrating the step of sticking a cell aggregate with the needle.
Figure 3D:
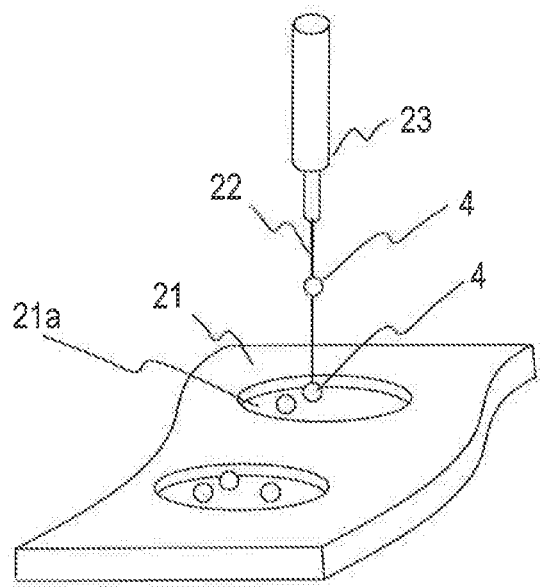
FIG. 3D is a view illustrating the step of sticking the cell aggregate with the needle.
Figure 4A:
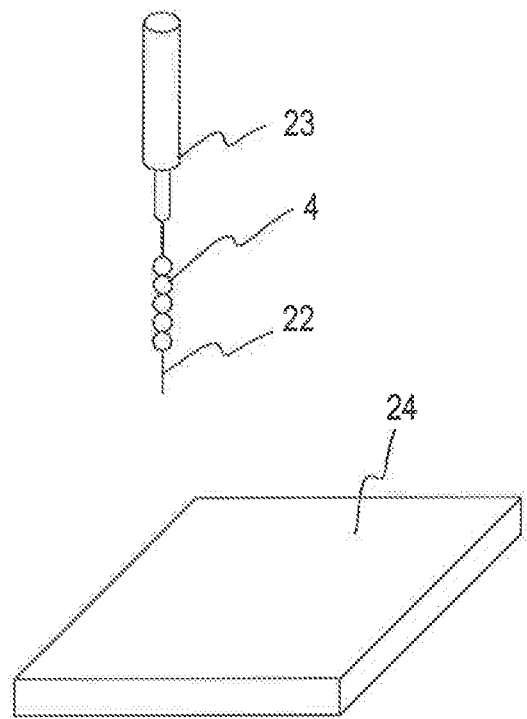
FIG. 4A is a view illustrating a step of disposing the needle after completing sticking of cell aggregates in a base unit.
Figure 4B:
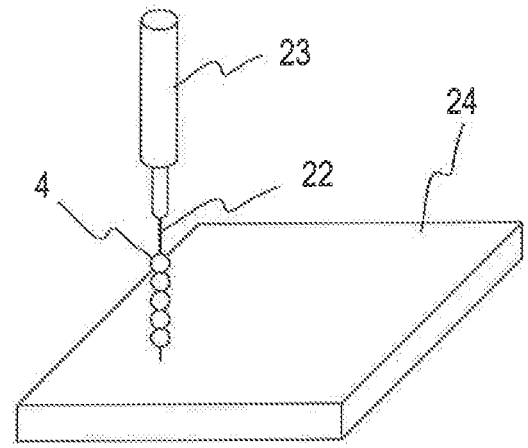
FIG. 4B is a view illustrating a step of disposing the needle after completing sticking of the cell aggregates in the base unit.
Figure 4C:
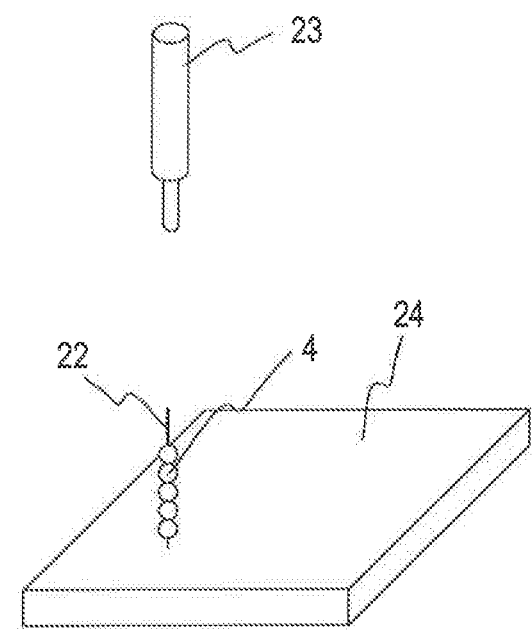
FIG. 4C is a view illustrating the step of disposing the needle after completing sticking of the cell aggregates in the base unit.
Figure 4D:
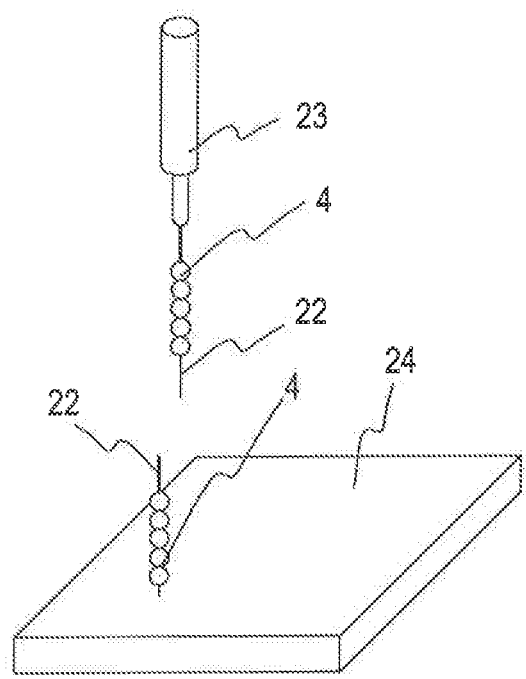
FIG. 4D is a view illustrating a step of disposing a needle after completing sticking of cell aggregates in the base unit.

First, a method for producing a cell structure of the present invention and a cell structure producing apparatus 1 that realizes the method will be described with use of FIG. 1 and FIG. 2. FIG. 1 illustrates the cell structure producing apparatus 1. FIG. 2 illustrates a configurational block diagram of the cell structure producing apparatus 1. The cell structure producing apparatus 1 includes a mechanism unit 2 and a circuit unit 3. A cell aggregate (spheroid) is formed as a spherical cell aggregate by culturing a large number of cells and aggregating the cells, and is transferred into a cell aggregate receive portion 21a of a cell tray 21 after a cultivation process and is held. The mechanism unit 2 includes a needle 22, a sticking unit 23 and a base unit 24. The mechanism unit 2 may include a detection unit 25. The circuit unit 3 includes a control unit 31, a processing unit 32 and a memory unit 33.

The cell tray 21 is a tray in which the cell aggregate receive portion 21a is disposed in a frame member. A cell aggregate is held in the cell aggregate receive portion 21a. In the cell aggregate receive portion 21a, at least one cell aggregate is included. The cell aggregate receive portion 21a can be a portion in which a porous material through which the needle 22 can easily penetrate such as unwoven fabric is disposed on a bottom surface of a hole, or a portion having a recess to be an escape portion for a tip end of the needle 22 in a bottom portion.

The needle 22 is a needle-shaped body elongated and having a pointed tip end formed from stainless steel or tungsten, for example, has a cell non-adherence property, rust resistance, and a low elution property, and has sufficient rigidity to stick a cell aggregate. A sectional diameter of the needle 22 has an arbitrary diameter with which the needle 22 does not break a cell aggregate when sticking the cell aggregate, and does not hinder fusion of the cell aggregates, and has a diameter of 50 micrometers to 300 micrometers. In the cell structure producing apparatus 1, a plurality of needles 22 are prepared. The plurality of needles 22 are stored in a needle cartridge (not illustrated), the sticking unit 23 moves to the needle cartridge, and the sticking unit 23 detachably holds one needle 22 from the needle cartridge. The sticking unit 23 is capable of moving in three axes directions that are two axes in a horizontal direction and one axis in a vertical direction on a base 26 by a vertical direction moving portion 23a, and horizontal direction moving portions 23b and 23c.

The base unit 24 is a base formed from a silicon material or the like, and is a member enabling the needle 22 to easily stick the member to stand by itself, and capable of holding the needle 22 so that the needle 22 stands by itself when the tip end of the needle 22 sticks the member. The sticking unit 23 is movable between over the cell aggregate receive portion 21a of the cell tray 21 and over the base unit 24.

The detection unit 25 is a light receiving element such as an optical sensor or an image pickup device such as a camera, and is capable of detecting a cell aggregate in the cell aggregate receive portion 21a. As the detection unit 25, it is possible to use detection means of various types if the detection means can recognize a cell aggregate. In the detection unit 25 of any type, a signal from the light receiving element or the image pickup device is stored in the memory unit 33. The processing unit 32 reads data of signals from the memory unit 33 and can acquire a contour of a cell aggregate. The data of the cell aggregate processed in the processing unit 32 is stored in the memory unit 33. The control unit 31 controls a position of the needle 22 by moving the sticking unit 23 based on the processing unit 32.

Next, with reference to FIG. 3A to FIG. 3D and FIG. 4A to FIG. 4D, how the needle 22 held by the sticking unit 23 operates with respect to the cell aggregate receive portion 21a holding a cell aggregate 4 and the base unit 24 in the cell structure producing apparatus 1 will be described. FIG. 3A to FIG. 3D are views illustrating steps of sticking the cell aggregate 4 with the needle 22. FIG. 4A to FIG. 4D are views illustrating steps of disposing the needle 22 after completing sticking the cell aggregate 4, in the base unit 24. First, the control unit 31 identifies a position of the cell aggregate 4 to be stuck. The control unit 31 moves the sticking unit 23 over the cell aggregate 4. The sticking unit 23 stands by in a standby position at a predetermined height. When the sticking unit 23 moves over the cell aggregate 4 to be stuck, the control unit 31 controls the sticking unit 23 to descend. The sticking unit 23 follows this, and descends with respect to the cell tray 21 to stick the cell aggregate 4 so that the needle 22 penetrates the cell aggregate 4. When the needle 22 is positioned in a position (descending position) at which the needle 22 descends by a predetermined descending amount, until the cell aggregate 4 is positioned in a predetermined position of the needle 22, the needle 22 penetrates the cell aggregate 4 and the cell aggregate 4 is positioned in a predetermined position of the needle 22. Thereafter, the control unit 31 controls the sticking unit 23 to ascend. The sticking unit 23 follows this, and the needle 22 ascends with respect to the cell tray 21. The control unit 31 moves the sticking unit 23 so that needle 22 that sticks the cell aggregate 4 is positioned over the cell aggregate 4 to be stuck next. By repeating this process, one or more cell aggregates 4 are stuck on the one needle 22.

Subsequently, when sticking of the one or more cell aggregates 4 onto the needle 22 is completed, the sticking unit 23 is moved so that the needle 22 on which the cell aggregates 4 are stuck is positioned over the base unit 24. The control unit 31 moves the sticking unit 23 to a predetermined position of the needle 22 over the base unit 24 calculated by the processing unit 32. When the sticking unit 23 completes movement over the predetermined position, the sticking unit 23 descends, and sticks the tip end of the needle 22 into the base unit 24 and disposes the needle 22. When the tip end of the needle 22 is stuck, the sticking unit 23 releases holding of the needle 22. At this time, such a mode can be adopted that the sticking unit 23 itself descends to temporarily stick the tip end of the needle 22 into the base unit 24, and a pressing portion disposed in the sticking unit 23 further sticks the needle 22 finally. The needle 22 stuck into the base unit 24 is disposed and held in the base unit 24 in a state where the needle 22 stands by itself to extend in the vertical direction. As for another needle 22, after sticking of the cell aggregates 4 onto the needle 22 is completed on the cell tray 21, the sticking unit 23 is moved to a predetermined position calculated in the processing unit 32 with respect to the needle 22, a tip end of the needle 22 is stuck into the base unit 24 similarly, and the needle 22 is disposed in the base unit 24 and is held.

Figure 5A:
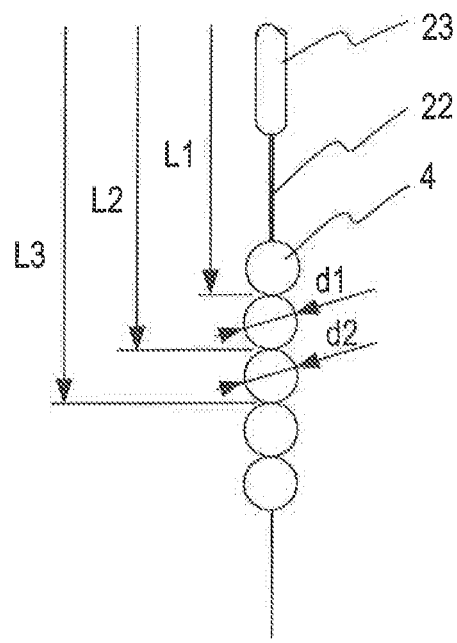
FIG. 5A is a view illustrating a positional relationship between the needle and cell aggregates at a time of sticking the cell aggregates.

With use of FIG. 5A and FIG. 5B, control of positions of the cell aggregates 4 to be stuck on the one needle 22 will be described. The position of the cell aggregate 4 to be stuck on the needle 22 is controlled by a descending amount of the sticking unit 23. FIG. 5A is a view illustrating a case where all the cell aggregates 4 to be stuck on the needle 22 are adjacent to one another. First, a length to the tip end of the needle 22 from a reference position is calculated in advance. When all of the cell aggregates 4 are stuck on the needle 22 to be adjacent to one another, a distance L1 to a position of the cell aggregate 4 at a tip end side of the needle 22 from an arbitrary reference position of the sticking unit 23 is calculated in advance. An amount obtained by subtracting a length of the distance L1 from the length to the tip end of the needle 22 from the reference position is the descending amount of the sticking unit 23. A position of a second cell aggregate 4 to be stuck to be adjacent to the cell aggregate 4 is a distance L2 obtained by adding a diameter d1 of the cell aggregate to the distance L1 from the reference position. Accordingly, an amount obtained by subtracting the distance L2 from a distance to the tip end of the needle 22 from the reference position is the descending amount of the sticking unit 23 with respect to the second cell aggregate 4. Further, likewise, a position of a third cell aggregate 4 to be stuck to be adjacent to the second cell aggregate 4 is a position of a distance L3 obtained by adding a diameter d2 of the cell aggregate to the distance L2 from the reference position, and an amount obtained by subtracting the distance L3 from the length to the tip end of the needle 22 from the reference position is the descending amount of the sticking unit 23 with respect to the third cell aggregate 4. Here, the diameters d1 and d2 of the cell aggregate 4 are actually different according to the cell aggregates, but can be controlled to substantially same lengths in a culturing stage, so that a same diameter is adopted to make the diameters uniform, that is, an average value is calculated, and the average value may be used. A similar process is repeated by a number of cell aggregates 4 to be stuck.

Figure 5B:
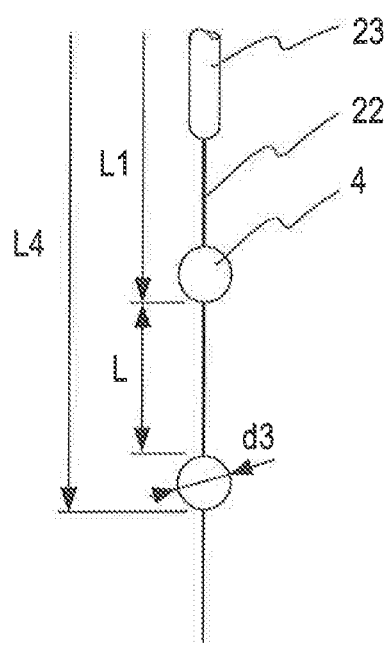
FIG. 5B is a view illustrating a positional relationship between the needle and cell aggregates at the time of sticking the cell aggregates.

FIG. 5B is a view of the cell aggregates 4 being stuck on the needle 22 so that the cell aggregates 4 are not adjacent to each other. First, the length to the tip end of the needle 22 from the reference position is calculated in advance. When the cell aggregates 4 are stuck not to be adjacent in the needle 22, the distance L1 to the position corresponding to the tip end side of the needle 22 in the cell aggregate 4 from the reference position is calculated in advance with respect to the first cell aggregate 4 first, and an amount of the difference from the length to the tip end of the needle 22 from the reference position is the descending amount of the sticking unit 23 with respect to the first cell aggregate 4. Next, when the second cell aggregate 4 is stuck by being separated from the first cell aggregate 4 with a space L, a distance L4 with a diameter d3 of the cell aggregate 4 being added is calculated, and an amount of the difference from the length to the tip end of the needle 22 from the reference position is the descending amount of the sticking unit 23 with respect to the second cell aggregate 4. In this case, the diameters d1 and d2 of the cell aggregates 4 can be controlled to substantially same lengths in the culturing stage although the diameters d1 and d2 are different actually, and therefore the diameters d1 and d2 can be calculated as the same diameters to be the uniform diameters.

Figure 6A:
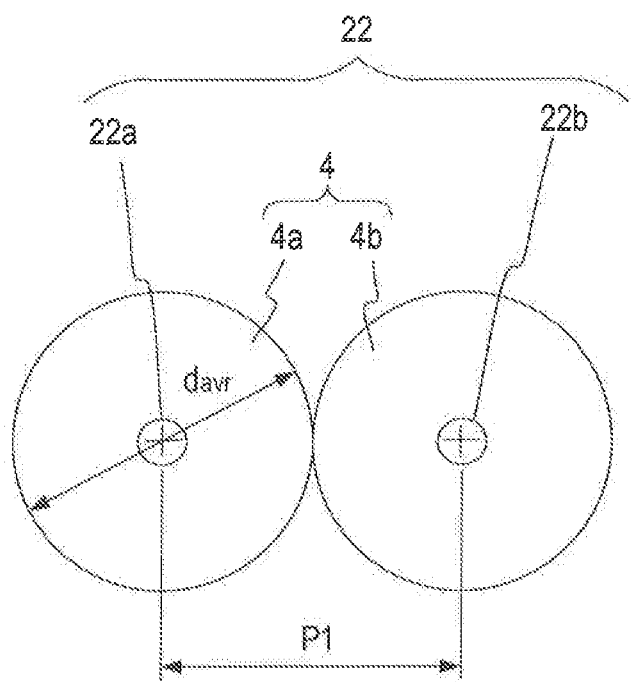
FIG. 6A is a view illustrating a relationship of a space between the cell aggregates stuck on the needle.
Figure 6B:
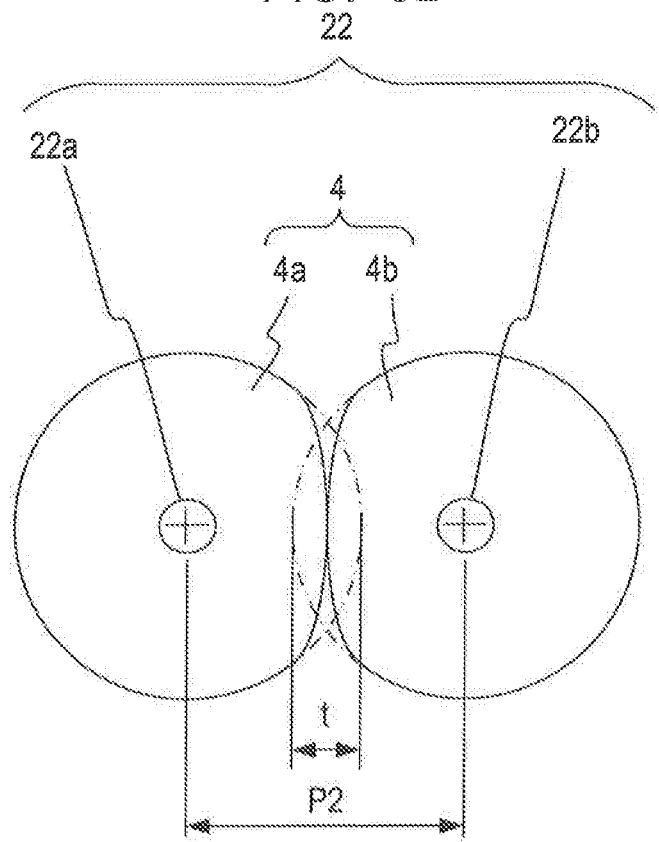
FIG. 6B is a view illustrating a relationship of the space of the cell aggregates stuck on the needle.
Figure 6C:
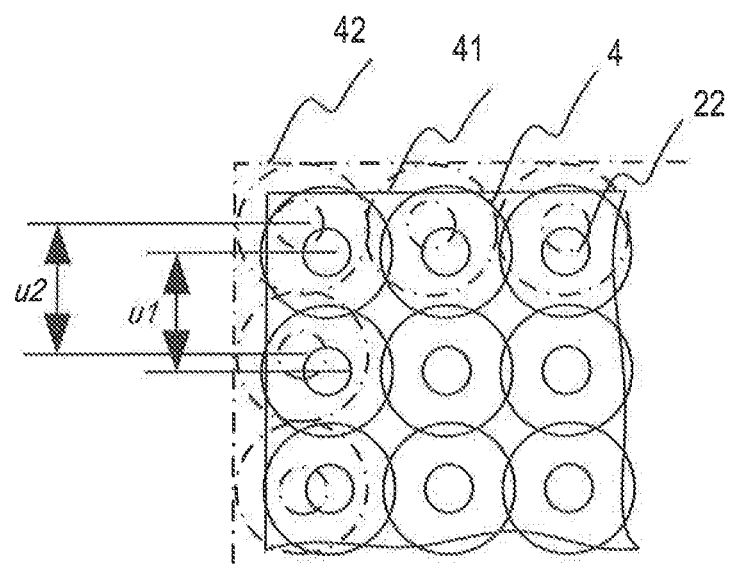
FIG. 6C is a view illustrating a concept of a method for setting spaces among cell aggregates.

The cell aggregates 4 stuck and adjacent in the one needle 22, and the cell aggregates 4 adjacent in the two adjacent needles 22 disposed in the base unit 24 are preferably in a state contacting with each other strongly to some extent. Therefore, an extent to which outer shapes of the cell aggregates 4 simply contact each other is insufficient, and a state where the adjacent cell aggregates 4 are in contact with each other at a predetermined compression rate is preferable. With use of FIG. 6A to FIG. 6C, a distance between a cell aggregate 4a and a cell aggregate 4b adjacent to each other will be described. FIG. 6A is a view illustrating a positional relationship in which the cell aggregates 4 touch each other. FIG. 6B is a view illustrating a preferable distance between the cell aggregates 4. FIG. 6C illustrates a relationship of compression rates at a time of determining a space dimension of the needles 22 to an outer shape to be the requirement to the cell aggregate 4. As in FIG. 6A, a distance P1 at which the cell aggregates 4 touch each other geometrically equals to twice as long as (diameter) a radius davr of the cell aggregate 4, and this corresponds to a minimum necessary distance to a space between a needle 22a and a needle 22b. However, in reality, it is preferable that the cell aggregates 4 are in contact with each other with a fixed pressure and contact area in order that the cell aggregate 4 fuses to the adjacent cell aggregate 4 in cultivation. Accordingly, a preferable space P2 between the cell aggregates 4 is preferably set at the distance P2 (P2=P1−t) obtained by subtracting a space t from the distance P1 which is an extent to which the cell aggregates 4 touch each other, and in the one needle 22, it is preferable to set the distance between the adjacent needle 22a and needle 22b at P2. This is defined as compression rate $\delta = P2/P1 = (P1-t/P1)$. The compression rate $\delta$ is determined so that a predetermined range is allowed depending on the cell aggregate 4, and is generally set in a range of 20% or less.

The compression rate is set as follows, for example. An outside dimension or an inner diameter dimension of a cell structure in a completed state desired to be produced finally is set as a dimension of the requirement. From the required dimension, a position of the needle 22 is determined. Here, a case where the outside dimension is set as the dimension of the requirement will be described as an example. For example, a space u1 of the needles 22 is determined as the compression rate $\delta$ with respect to an outer shape 41 of the cell structure in the completed state desired to be produced in FIG. 6C. That is, a position obtained by subtracting the radius of the cell aggregate 4 from the outside dimension is a center position of the needle 22 at an outermost portion. The distance of the needles 22 is set, with which the compression rate $\delta$ that is allowed when a width of the center position of the needle 22 at the outermost portion is divided by the diameter of the cell aggregate 4 is kept. It is preferable to select the distance of the needles 22 with the optimal compression rate $\delta$ which is not high or low, for example, 20%. However, with respect to an outer shape 42 of the cell structure of the requirement slightly different in dimension, the space of the needles 22 cannot be determined with the same compression rate $\delta$ as the space u1 of the needles 22 being kept, unless in the difference in the requirement, a multiple of the space u1 of the needles 22 is kept. Accordingly, in the case like this, there arises necessity to set the space by reducing the compression rate $\delta$ within an allowable range. That is, in the case like FIG. 6C, when the outer shape 41 and the outer shape 42 are compared, with respect to the space u1 of the needle 22 to the outer shape 41, the space of the needles 22 at the same compression rate $\delta$ cannot be kept, so that the compression rate $\delta$ is reduced within the allowable range, and the space dimension of the needles 22 adapted to the outside dimension is set so that the space u1 of the needles 22 is made the space u2.

Figure 7A:
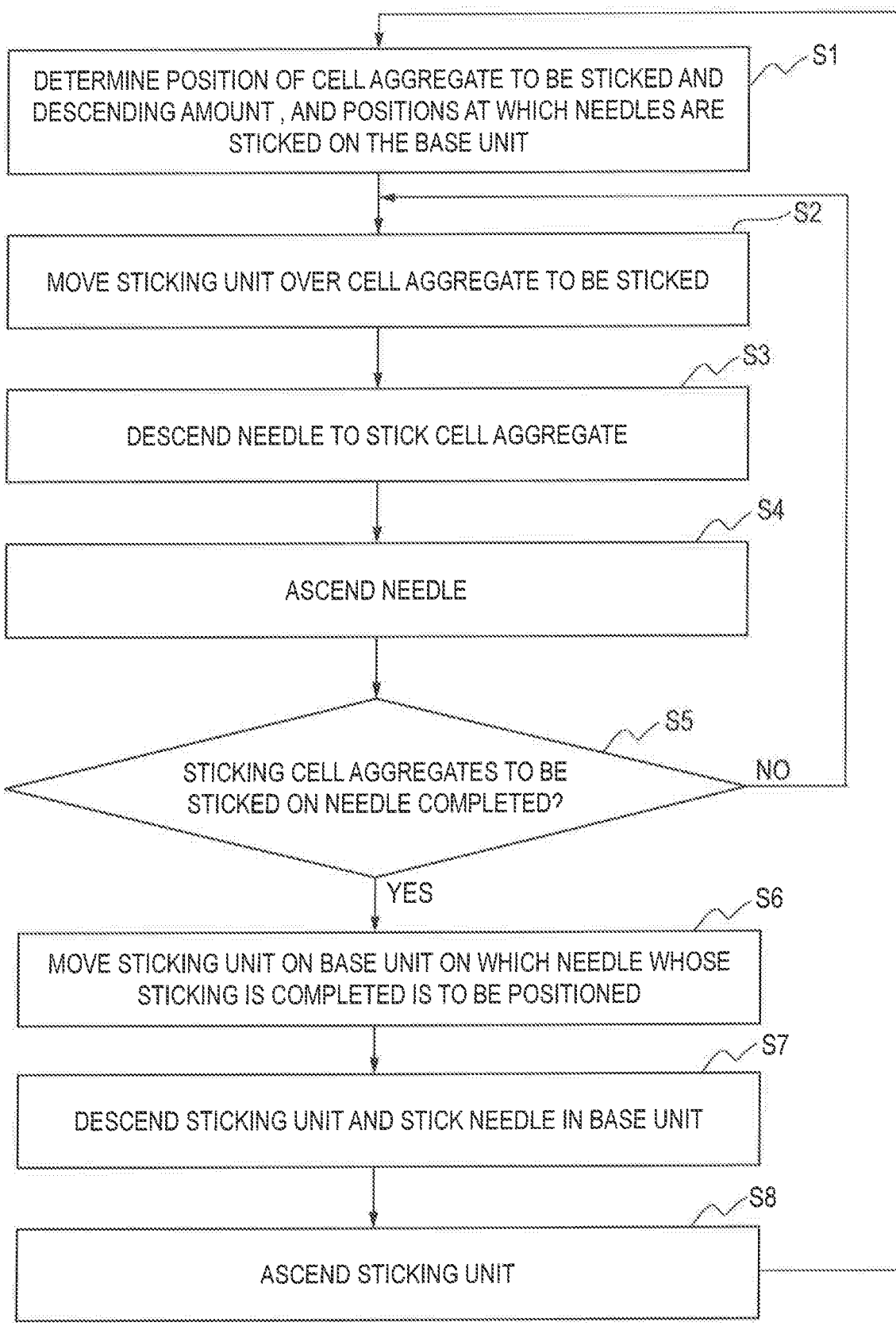
FIG. 7A is a flowchart of a process of sticking a cell aggregate and disposing the cell aggregate on the needle.

Subsequently, with reference to FIG. 7A and FIG. 7B, a method for producing the cell structure by sticking the cell aggregates 4 by the cell structure producing apparatus 1 will be described. FIG. 7A illustrates a flowchart of respective processes of the method for producing the cell structure by sticking the cell aggregates 4.

First, a position and a size of the cell aggregate 4 to be stuck are identified, and the descending amount of the needle 22 is determined. A determination step (S1) of determining positions of the respective needles in which the needles 22 are disposed on the base unit 24 is executed. In this step, as in the calculation, with respect to the descending amount in the one needle 22, and the distance between the needle 22a and the needle 22b which are adjacent to each other, the descending amount and the distance are set as the distance obtained by multiplying the diameter of the cell aggregate 4 by the compression rate $\delta$. In this step, how many cell aggregates 4 are stuck and in which positions of the needle 22 the cell aggregates 4 are stuck are determined for the arbitrary one needle 22 of the plurality of needles 22 which are prepared. Subsequently, in this step, the disposition position in which the needle 22 is disposed on the base unit 24 is determined for each of the needles 22 on which the cell aggregates 4 are stuck.

Subsequently, a step (S2) of moving the sticking unit 23 identified in the previous step over the cell aggregate 4 to be stuck on the cell aggregate receive portion 21a is executed. Then, a step (S3) of causing the needle 22 to descend by the descending amount calculated in the previous step, and causing the needle 22 to penetrate the cell aggregate 4 is executed. After the needle 22 completes descending by the predetermined descending amount, a step (S4) of causing the needle 22 to ascend to the standby position is executed. Until the predetermined number of cell aggregates 4 are stuck in the predetermined position on the needle 22, step (S2) to step (S4) are repeated (S5). After the predetermined number of cell aggregates 4 are stuck onto the needle 22, the sticking unit 23 is moved to the predetermined position on the base unit 24 determined in advance in the determination step (S1) (S6). Subsequently, the sticking unit 23 is caused to descend by the predetermined amount, and the tip end of the needle 22 is stuck into the base unit 24 (S7). After the tip end of the needle 22 is stuck in the base unit 24, the sticking unit 23 is caused to ascend by the predetermined amount (S8).

The determination step (S1) determines the position and the size of the cell aggregate 4 to be stuck. FIG. 7B illustrates a flowchart of a part of the above in which data about the position of the cell aggregate 4 to be stuck is processed. First, the one cell aggregate receive portion 21a of the cell tray 21 for which sticking is performed is identified (S101). In the detection unit 25, the cell aggregate 4 on the cell aggregate receive portion 21a is recognized. When the detection unit 25 is a camera, a contour of the cell aggregate 4 is recognized by video (S102). Based on this, the center position, for example, the gravitational position of the cell aggregate 4 to be stuck is identified, and the diameter of the cell aggregate 4 is calculated. This may be performed to a plurality of cell aggregates 4. The diameters of the plurality of cell aggregates 4 are processed statistically and a representative diameter is determined. For example, an average value of the diameters of the plurality of cell aggregates 4 may be adopted (S103). Further, the diameter of the cell aggregates 4 can be a value input by a user based on the diameter of the cell aggregate 4 measured in advance. On the cell aggregate receive portion 21a, the single cell aggregate 4 may be placed, or a plurality of cell aggregates 4 may be placed. In the case of the former, the center position of the single cell aggregate 4 on the cell aggregate receive portion 21a is identified, and in the case of the latter, center positions of all of the cell aggregates 4 on the cell aggregates receive portion 21a, and an order of the cell aggregates 4 to be stuck are determined. The data of the size of the cell aggregate 4 is stored in the memory unit 33, and it is also possible to calculate the average value davr statistically from the value of the diameter of the cell aggregate 4. A position obtained by subtracting the radius of the cell aggregate 4 from the outside dimension of the cell structure to be produced finally is determined as a trace line of the center position of the needle 22 to be the outermost portion (S104). Subsequently, the space of the needles 22 is determined as described above by the diameter and the compression rate $\delta$ of the cell aggregate 4 (S105).

Figure 8:
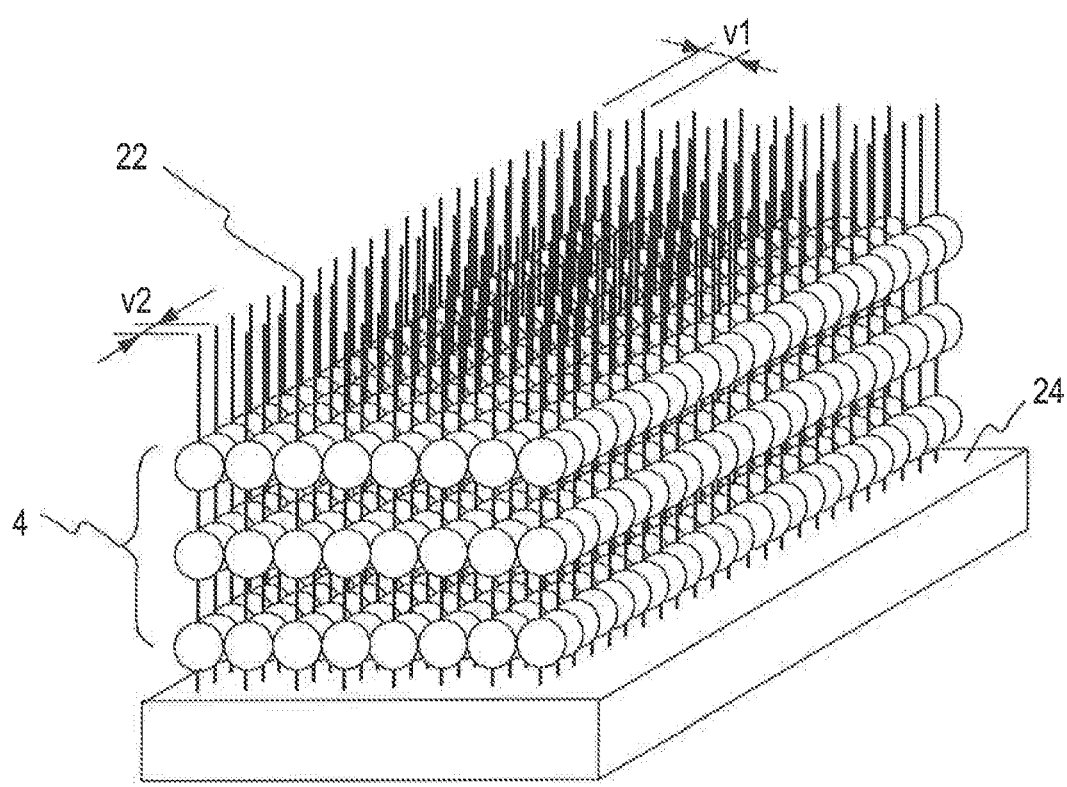
FIG. 8 is a view illustrating an example of disposition of needles for cell sheet structure production.

Subsequently, with reference to FIG. 8 to FIG. 11, a disposition example of the needles 22 for the cell structure to be produced will be described. FIG. 8 is disposition of the needles 22 for producing a plurality of cell structure sheets at one time. In this case, a space v1 and a space v2 of the needles 22 are respectively equal spaces. As for the space v1 and the space v2 of the needles 22, the space v1 and the space v2 are determined by setting the compression rates $\delta$ respectively in response to the outer shape required in the final completion state. Further, as illustrated in FIG. 8, a plurality of sheets can be formed at one time if the cell aggregates 4 are disposed with spaces left in the respective needles 22.

Figure 9A:
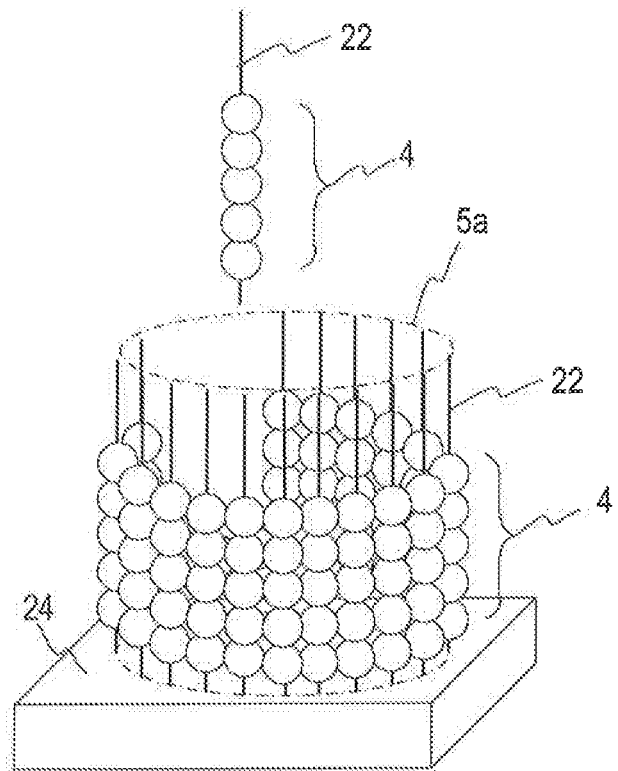
FIG. 9A is a schematic view of a process of an example of disposition of needles for tubular cell structure production.
Figure 9B:
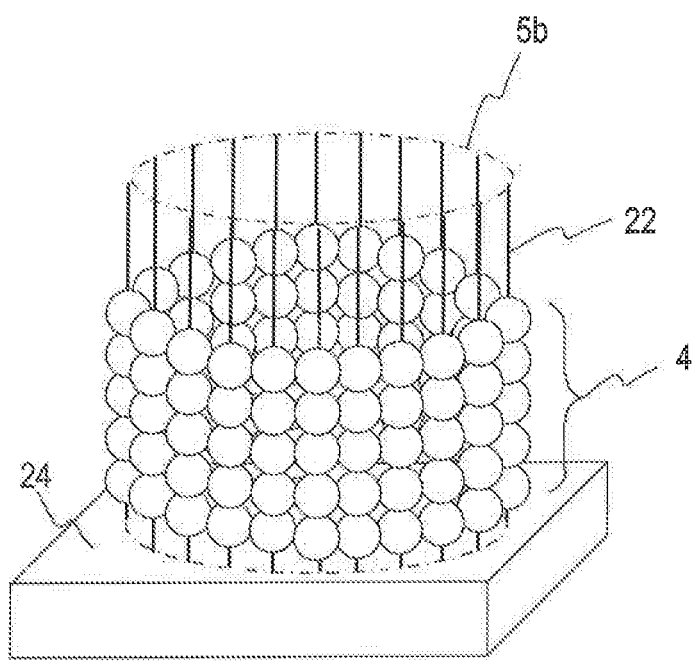
FIG. 9B is a schematic view of the process of an example of disposition of the needles for tubular cell structure production.
Figure 10A:
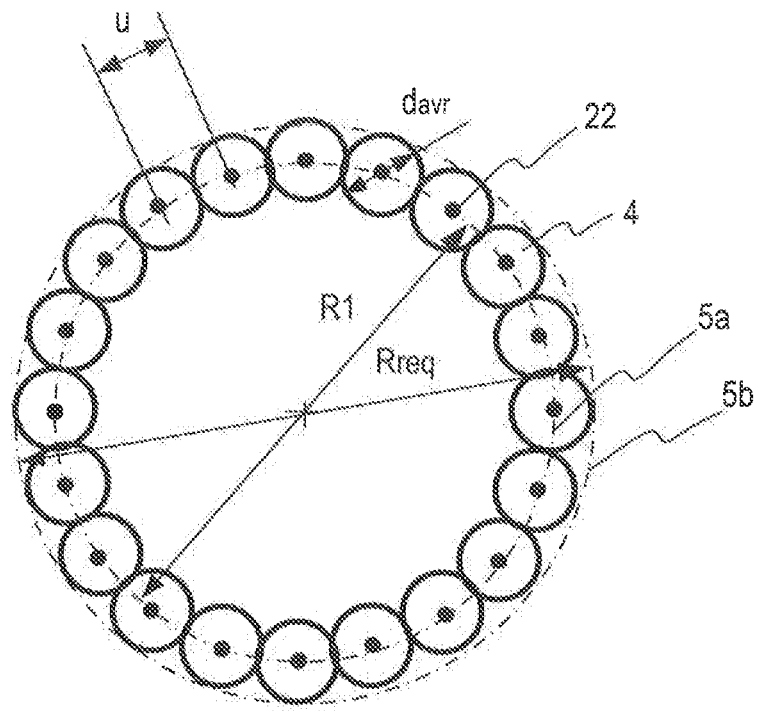
FIG. 10A is a cell aggregate configuration diagram in the example of disposition of the needles for tubular cell structure production.
Figure 10B:
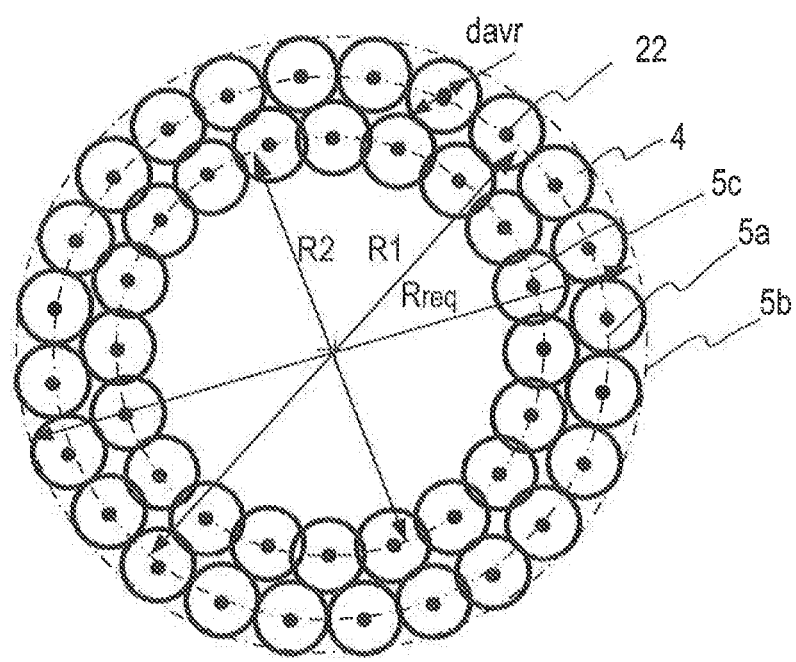
FIG. 10B is a cell aggregate configuration diagram in the example of disposition of the needles for tubular cell structure production by a double cell aggregate configuration.

Subsequently, FIG. 9A and FIG. 9B are each disposition of the needles 22 in the case of producing a hollow tubular cell structure from which an accurate circle is required as a section, and the needles 22 are disposed so that a center axis of a hollow tube extends in a normal direction of the base unit 24. FIG. 10A illustrates a sectional view seen from a direction along the center axis of the hollow tube in the case of FIG. 9B. In this case, as illustrated in FIG. 9A, the needles 22 that stick the cell aggregates 4 are disposed by being stuck in the base unit 24 annularly in a predetermined order so that a trace line 5 of the needles 22 forms a circle. As for the predetermined order, disposition is performed in a most efficient order. That is, in a plurality of needles 22 configuring the annular shape, disposition is not necessarily performed in the order of the adjacent needles 22, but disposition may be performed along a direction in a plane of the base unit 24. The needles 22 are disposed so that the hollow tube is formed as in FIG. 9B. Here, the case where the outside dimension is set as the dimension of the requirement is explained as an example, but an inner diameter dimension may be set as the dimension of the requirement. When this is seen from the center axis direction of the tube, the requirement of the tubular cell structure is determined by a diameter Rreq of an outer shape $5b$ of the tube, so that a trace line $5a$ obtained by subtracting the diameter davr of the cell aggregate 4 from the diameter dimension is a circle of a diameter R1. The needles 22 are disposed on the trace line $5a$ of the diameter R1. At this time, a length of a circumference is $\pi R1$, so that when the length of the circumference is divided by the diameter davr of the cell aggregate 4, a simple space of the needles 22 can be calculated. Subsequently, by multiplying the space by the compression rate $\delta$, a space u of the needles 22 is determined. FIG. 10B is a disposition example of the needles 22 in a case where the cell aggregates 4 are doubly disposed in FIG. 10A. When a plurality of combinations are conceivable with respect to a relationship between the compression rate $\delta$ and the space u of the needles 22, an optimum one is determined. For example, when the outer diameter dimension is set as the dimension of the requirement, a combination in which the compression rate $\delta$ is minimum is selected, and when the inner diameter dimension is set as the dimension of the requirement, a combination in which the compression rate $\delta$ is maximum can be selected. In this case, a trace line $5c$ is disposed further inside the trace line $5a$, so that a diameter R2 obtained by subtracting twice as large as the diameter davr of the cell aggregate 4 is a diameter of an inner tube. A trace line $5c$ is also calculated similarly to the trace line $5a$. Since the trace line $5c$ is a circle of a diameter R2, a length of a circumference is $\pi R2$ from this, so that when the length of the circumference is divided by the diameter davr of the cell aggregate 4, a simple space of the needles 22 can be calculated, and the space of the needles 22 is determined with the compression rate $\delta$ taken into consideration. When a plurality of combinations are conceivable with respect to the relationship between the compression rate $\delta$ and the space u of the needles 22, an optimum combination is determined. In this case, when the inner diameter dimension is set as the dimension of the requirement, a combination in which the compression rate $\delta$ is maximum can be selected.

Figure 11:
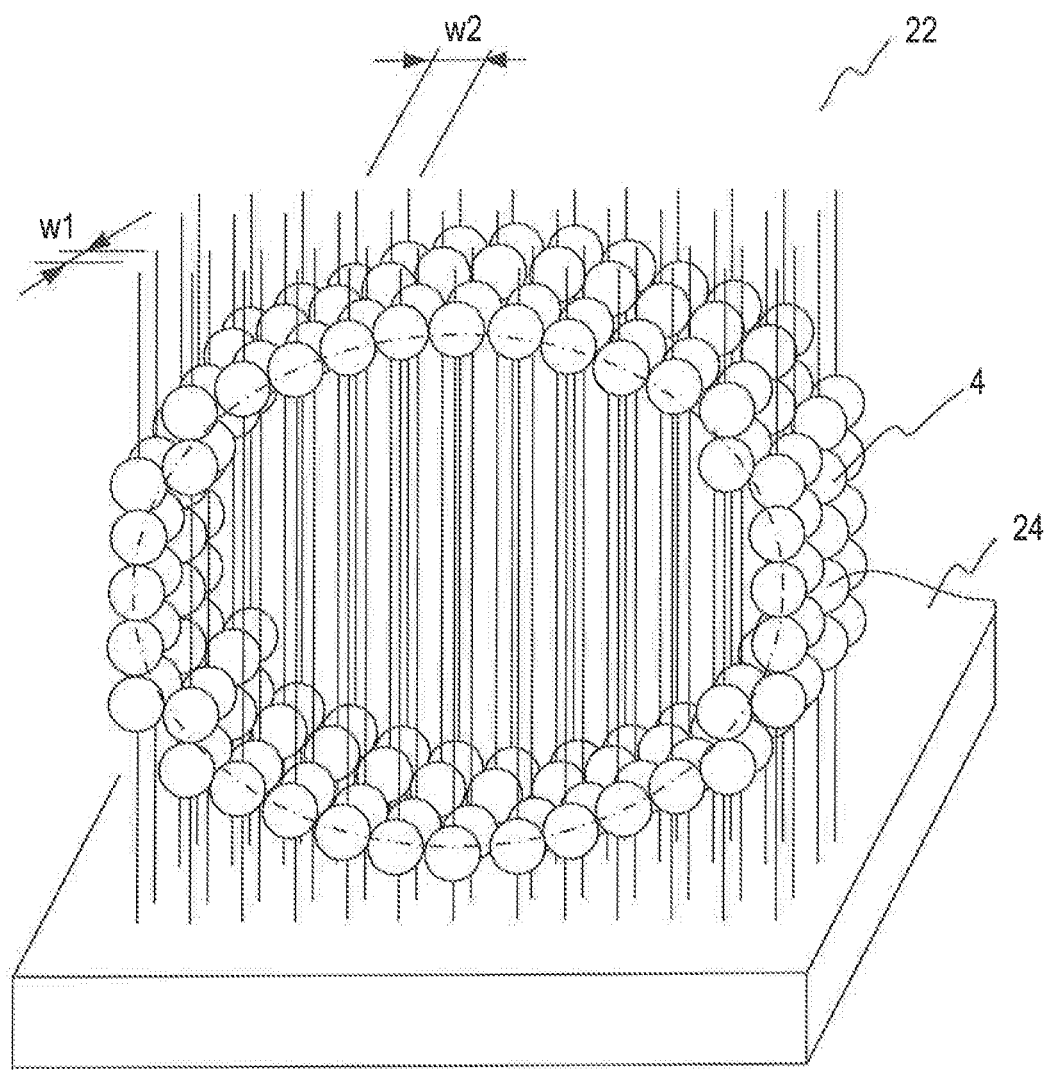
FIG. 11 is a view illustrating another example of disposition of needles for tubular cell structure production.

FIG. 11 is a view in which the needles 22 are disposed so that the center axis of the hollow tube becomes parallel with the base unit 24. This case is similar to the case in FIG. 9B because the cell structure can be formed as a conduit having a hollow part, but as long as the needles 22 can be continuously disposed, a long hollow tubular cell structure can be produced without limitation to a length thereof.

REFERENCE SIGNS LIST 1 cell structure producing apparatus
2 mechanism unit
3 circuit unit
4 cell aggregate
5 trace line
21 cell tray
22 needle
23 sticking unit
24 base unit
25 detection unit
31 control unit
32 processing unit
33 memory unit

The invention claimed is:

1. A cell structure producing apparatus comprising:
   needles each elongated and having a pointed tip end;
   a sticking unit configured to detachably hold an end portion of each of the needles, the end portion being an opposite side of the tip end of each of the needles, descend the each of the needles with respect to a cell tray in which cell aggregates are held, stick and penetrate each of the cell aggregates with the tip end, and ascend the needle after sticking, at least one time or more;
   a base unit having a surface capable of receiving the tip end to hold the needles, onto which the tip end of the each of the needles is stuck; and
   a control unit configured to move the sticking unit so that for the each of the needles, each of the needles sticking the cell aggregates is positioned at a predetermined position over the base unit, descend each of the needles by a predetermined amount to stick the tip end into the base unit at the predetermined position on the base unit, and control the sticking unit so that the sticking unit releases the each of the needles after the tip end is stuck in the base unit, to align the needles on the base unit,
   wherein the predetermined position is a position where a distance among the each of the needles held in the base unit is kept by a predetermined distance.

2. A cell structure producing apparatus according to claim 1,
   wherein the predetermined amount is an amount by which heights of cell aggregates which are stuck, from the surface of the base unit are to be the same, in the each of the needles.

3. A cell structure producing apparatus according to claim 1,
   wherein the predetermined distance is a distance obtained by multiplying a diameter of each of the cell aggregates by a predetermined compression rate, the predetermined distance being shorter than the diameter of each of the cell aggregates.

4. A cell structure producing apparatus according to claim 3,
   wherein a value of the diameter of the each of the cell aggregates is input into the control system by a user.

5. A cell structure producing apparatus according to claim 3, wherein the cell structure producing apparatus has a detection unit configured to detect shapes of the cell aggregates held in the cell tray, and a diameter of the each of the cell aggregates is an average diameter of the cell aggregates calculated based on measured values from a result detected by the detection unit.

6. A cell structure producing apparatus according to claim 1, wherein the alignment is alignment in which distances are equal distances that are the predetermined distances in two orthogonal directions, on the base unit.

7. A cell structure producing apparatus according to claim 4, wherein the needles stuck are aligned in a circle on the base unit, so that a central axis of the circle is in a direction perpendicular to the base unit.

8. A cell structure producing apparatus according to claim 7, wherein the needles stuck are aligned in the circle to produce the cell structure which has a predetermined outer diameter and a predetermined inner diameter, and a number of the needles is determined by i) dividing, by the value of the diameter of the cell aggregate, a circumference of a circle having a diameter obtained by subtracting a half of the value of the diameter of the cell aggregate from the predetermined outer diameter of the cell structure to be produced, or ii) dividing, by the value of the diameter of the cell aggregate, a circumference of a circle having a diameter obtained by adding the half of the value of the diameter of the cell aggregate to the predetermined inner diameter of the cell structure to be produced.

9. A cell structure producing apparatus according to claim 1, wherein the needles are aligned on the base unit so that the cell aggregates stuck on the needles are arranged to form a circle as a cross section of a cylindrical cell structure with a center axis being in a direction parallel with a surface of the base unit.

10. A method for producing a cell structure by a cell structure producing apparatus including:

needles each elongated and having a pointed tip end, a sticking unit configured to move the plurality of needles, and a base unit having a surface capable of receiving the tip end to hold the needles, onto which the tip end of the each of the needles is stuck, the method comprising:

a sticking step of, with respect to one of the needles, detachably keeping hold of an end portion at an opposite side of the tip end of the one of the needles, causing the one of the needles to descend with respect to a cell tray in which a cell aggregate is held, sticking and penetrating the cell aggregate with the tip end, and causing the one of the needles to ascend after sticking, at least one time or more; and disposing step of moving the one of the needles on which the cell aggregate is stuck to a predetermined position over the base unit, after the sticking step, causing the one of the needles to descend by a predetermined amount to stick the tip end into the base unit in the predetermined position of the base unit, and releasing the hold after the tip end is stuck in the base unit, the method performing alignment of the needles by repeatedly performing the sticking step and the disposing step to all of the needles so that each of distances among the needles held in the base unit becomes a predetermined distance.

11. A method for producing a cell structure according to claim 10, wherein the predetermined amount is an amount by which heights of cell aggregates which are stuck, from the surface of the base unit are to be the same, in the each of the needles.

12. A method for producing a cell structure according to claim 10, wherein the predetermined distance is a distance obtained by multiplying a diameter of each of the cell aggregates by a predetermined compression rate, the predetermined distance being shorter than the diameter of each of the cell aggregates.

13. A method for producing a cell structure according to claim 12, wherein a value of the diameter of the each of the cell aggregates is input into the control system by a user.

14. A method for producing a cell structure according to claim 12, wherein the cell structure producing apparatus has a detection unit configured to detect shapes of the cell aggregates held in the cell tray, and the method comprising a step of calculating an average diameter of the cell aggregates based on measured values of a result of the shapes of the cell aggregates detected by the detection unit, and setting the average diameter as the diameter of the cell aggregate.

15. A method for producing a cell structure according to claim 10, wherein the alignment is alignment in which distances are equal distances that are the predetermined distances in two orthogonal directions, on the base unit.

16. A method for producing a cell structure according to claim 13, wherein the needles stuck are aligned in a circle on the base unit, so that a central axis of the circle is in a direction perpendicular to the base unit.

17. A method for producing a cell structure according to claim 16, wherein the needles stuck are aligned in the circle to produce the cell structure which has a predetermined outer diameter and a predetermined inner diameter, and a number of the needles is determined by i) dividing, by the value of the diameter of the cell aggregate, a circumference of a circle having a diameter obtained by subtracting a half of the value of the diameter of the cell aggregate from the predetermined outer diameter of the cell structure to be produced, or ii) dividing, by the value of the diameter of the cell aggregate, a circumference of a circle having a diameter obtained by adding the half of the value of the diameter of the cell aggregate to the predetermined inner diameter of the cell structure to be produced.

18. A method for producing a cell structure according to claim 10, wherein the needles are aligned on the base unit so that the cell aggregates stuck on the needles are arranged to form a circle as a cross section of a cylindrical cell structure with a center axis being in a direction parallel with a surface of the base unit.

* * * * *